United States Patent [19]

Gaut

[11] Patent Number: 5,430,049

[45] Date of Patent: Jul. 4, 1995

[54] TREATING HYPERPROLIFERATIVE DISORDERS

[76] Inventor: Zane N. Gaut, 51 Mountain Ave., Warren, N.J. 07059

[21] Appl. No.: 163,614

[22] Filed: Dec. 8, 1993

[51] Int. Cl.$^6$ .............................................. A61K 31/40
[52] U.S. Cl. ..................... 514/410; 514/214
[58] Field of Search ................. 514/410, 214

[56] References Cited

U.S. PATENT DOCUMENTS

| | | | |
|---|---|---|---|
| 4,725,596 | 2/1988 | Friary et al. | 514/214 |
| 5,182,289 | 1/1993 | Ting et al. | 514/278 |
| 5,264,578 | 11/1993 | Chandraratna | 546/269 |

OTHER PUBLICATIONS

"Inhibition of Nicotinic Acid Metabolism in Human Blood Platelets by Nicotinic Acid Analogs and Nonsteroidal Antiinflammatory Drugs" Gaut, 1994.

"Asprin in the Prevention of Colorectal Cancer" Editorials, Aug. 1994, vol. 121, No. 4, pp. 303–304.

Annals of Internal Medicine, Aug. 1994, vol. 121, No. 4, "Asprin Use and the Risk for Colorectal Cancer and . . ." pp. 241–246.

Possible Publiction in the Annuals: "Asprin Use and Adenoma in Male Health Professionals", Zane N. Gaut, M.D., Ph.D., 1994.

Drug Therapy, Saven and Piro, vol. 330, No. 10, Mar. 10, 1994, pp. 691–698 (1993).

Cancer Research, vol. 53, pp. 1322–1327; Mar. 15, 1993; "Aspirin Use and Risk of Fatal Cancer"; Michael J. Thun, et al.

The New England Journal of Medicine, 1991, vol. 325, No. 23, Dec. 5, 1991, pp. 1593–1596; "Aspirin Use and Reduced Risk of Fatal Colon Cancer"; Michael J. Thun, et al.

Cancer Research, vol. 53, Dec. 15, 1993; "Correspondence re M. J. Thun et al. Aspirin Use and Risk of Fatal Cancer . . ."; Zane N. Gaut; p. 6074.

*Primary Examiner*—Arthur C. Prescott
*Attorney, Agent, or Firm*—Sprung Horn Kramer & Woods

[57] ABSTRACT

This invention describes a method for the treatment of a patient afflicted with a hyperproliferative disorder which comprises administering to a patient a effective amount of a compound which is an analogue of nicotinic acid and inhibits nicotinic acid metabolism in vitro in human platelets. Additionally, a method for determining the effectiveness of various compounds in treating a hyperproliferative disorder is described.

11 Claims, No Drawings

TREATING HYPERPROLIFERATIVE DISORDERS

The present invention relates to the treatment of patients afflicted with hyperproliferative disorders and for determining the effectiveness of various compounds therefor.

BACKGROUND OF THE INVENTION

The Preiss-Handler Pathway comprised the following sequence:
1. Nicotinic Acid + phosphoribosylpyrophosphate = Nicotinic Acid Mononucleotide (NaMN) + Pyrophosphate.
2. Nicotinic Acid Mononucleotide + ATP = Nicotinic Acid Adenine Dinucleotide (NaAD) + Pyrophosphate.
3. Nicotinic Acid Adenine Dinucleotide + Glutamine + ATP = Nicotinamide Adenine Dinucleotide (NAD) + Glutamate + AMP + Pyrophosphate.
4. Nicotinamide Adenine Dinucleotide + ATP = Nicotinamide Adenine Dinucleotide Phosphate (NADP) + ADP.

Nicotinic acid metabolism to nicotinic acid mononucleotide, NAD, and NADP (the Preiss-Handler Pathway) had been assessed in the human blood platelet, platelet lysate, the human red blood cell, and the rat liver slice.

In the early 1970's, Hoffman-LaRoche chemists synthesized several analogues of nicotinic acid in an effort to maximize antilipemic activity and minimize side effects. These and other analogues of nicotinic acid were assessed as inhibitors of the Preiss-Handler Pathway along with non-steroidal antiinflamatory drugs (NSAIDs)—especially salicylate and aspirin.

In 1991 and 1993, reports appeared in the *New England Journal of Medicine* and *Cancer Research* which indicated that the administration of aspirin, increased survival time of cancer patients.

Possibly, the mechanism was inhibition of the first reaction in the pathway of Preiss and Handler. Such inhibition could decrease the cellular levels of NAD and NADP, which are the first proton and electron carriers for energy production in virtually all cells.

BROAD DESCRIPTION OF THE INVENTION

In accordance with the invention there are administered to patients afflicted with hyperproliferative disorders, i.e. disorders which require relatively large quantities of energy and high rate of ATP production for rapid proliferation and also rely heavily on the glycolytic pathway, which is NADP dependent, amounts of particular compounds which retard energy production. These compounds reduce the rate of cellular proliferation, in effect starving such cells to death. Thus, compounds which inhibit nicotinic acid metabolism in vitro in human platelets will retard the energy production by inhibiting nicotinic acid metabolism.

The active materials, described more fully hereinbelow, are analogues of nicotinic acid. Representative hyperproliferative disorders include psoriasis, psoriatic arthritis, rheumatoid arthritis, cutaneous hyperkeratoses, inflammatory bowel disease and cancers of the gastrointestinal tract, preferably colon carcinoma.

Suitable compounds in accordance with the invention for competing and interfering with the normal functioning of nicotinic acid in the Preiss-Handler Pathway, include optionally substituted pyridine, optionally substituted pyrazine, optionally substituted 1,3,5-triazine, optionally substituted 1,2,4-triazine, optionally substituted 1,2,3-triazine, substituted 2-pyridylcarbinol, substituted 3-pyridylcarbinol, substituted 3-pyridylcarboxaldehyde, optionally substituted 4-pyridylcarboxaldehyde, optionally substituted nicotinuric acid and optionally substituted nicotinic acid N-oxide wherein the substituents are selected from the group consisting of amino, halo, carboxy, mercapto, and hydroxy as well as the non-toxic salts, esters, amide, aldehydes and alcoholic reductant products of the corresponding acids and the $C_1$–$C_{22}$ branched and unbranched ethers of said alcoholic products.

A more preferred series of compounds include:
2-hydroxynicotinic acid
4-hydroxynicotinic acid
2-fluoronicotinic acid
3,5-pyridyldicarboxylic acid
4-pyridylcarboxaldehyde
4-chloronicotinic acid
5-hydroxynicotinic acid
6-chloronicotinic acid
2,3-pyridyldicarboxylic acid
pyridine
5-chloronicotinic acid
nicotinuric acid
nicotinic acid-N-oxide
ethyl-2-hydroxynicotinate
2-hydroxynicotinamide
pyrazinoic acid and
triazinoic acids as well as 2,4,5 and 6-halo derivatives thereof where chemically possible and especially 2-F analogues where possible, as well as non-toxic salts, esters, amides, aldehydes and alcoholic reductant products of the corresponding acids, and the $C_1$–$C_{22}$ branched and unbranched hydrocarbyl ethers of said alcoholic products.

A preferred subgroup of such compounds comprise compounds which are halosubstituted and a more preferred subgroup comprises compounds wherein the halogen is fluorine. A most preferred subgroup is those analogues which are substituted in the 2 or 6 position by fluorine. A most preferred compound is 2-amino-4-hydroxy-nicotinic acid.

Another aspect of the present invention is to develop a screening assay to determine whether a compound would be effective in treating hyperproliferative disorders. This assay comprises the steps of (1) incubating the test compound with intact human platelets or the lysates thereof in the presence of nicotinic acid and phosphoribosylpyrophosphate under conditions such that the nicotinic acid would be converted to NaMN, NaAD, NAD and NADP; and (2) determining the extent of the inhibition caused by said compound on said conversion by measuring the quantity of at least one of said products produced in the reaction and comparing this quantity against the amount of said product produced in said conversion when only nicotinic acid is present.

The lower the rate of conversion relative to nicotinic acid alone as a control, the greater the likely usefulness in the treatment of the hyperproliferative disorder.

For the treatment of a hyperproliferative disorder such as psoriasis, for example, a dose of from about 10 to 10,000 mg/day, preferably about 100 to 5,000 mg/day and more preferably about 200 to 2,000 mg/day is suitable. However, in a particular case the dosage may be higher or lower, as determined by the physician in charge.

For the treatment of ulcerative colitis, an inflammatory bowel disease, a solution suitable for an enema is prepared. Typically 0.1–5.0% of the active compound is dissolved in normal saline and the pH is adjusted to 7.4. This formulation may be administered orally and parenterally as well as by suppository.

The active material may be administered one or more times per day orally, rectally, by injection or topically. For prolonged action and reduced number of applications the active material can be administered as a mixture of bound compounds of different rates of release within the body, e.g. as salts or adducts of differing solubilities.

Advantageously it is administered at least about ten times over a course of about ten days, e.g. daily, but it can be administered intermittently on alternate days. For certain conditions and their stage in the patient the treatment can run at least one month, or even a year or more, or virtually for the patient's life. While not certain of the mechanism, as stated hereinabove, it is believed the active material competes with nicotinic acid in the first step of the Preiss-Handler Pathway and thus reduces the amount of nicotinic acid mononucleotide formed and, in turn, ultimately the amount of NAD and NADP.

The active material can be administered as a solid or liquid with conventional adjuvants and/or fillers, e.g. pH controlling agents, buffers, solvents, tabletting agents, and the like. Representative materials of that kind include barium sulfate, calcium oxide, silica, ethylene glycol, polypropylene glycol, polyvinyl pyrrolidone, and the like.

The foregoing treatment can be alone or in conjunction with other treatments of the particular condition, whether working by the same or a different mechanism. In particular cases the conjoint treatment may exert a synergistic effect, i.e. more than the additive effects of the individual treatments alone.

As previously noted, the concept underlying the present invention can be employed to determine the effectiveness of any compound, new or old, to treat hyperproliferative diseases, relative to nicotinic acid. For such a determination, the assay is calibrated by mixing 1.0–50.0 $\mu$M solution of $^{14}$C-nicotinic acid with 30–50 mg, wet weight, of human blood platelets in calcium-free and magnesium-free Krebs-Ringer bicarbonate buffer. The mixture is incubated for 10–100 minutes in an atmosphere containing 95% $O_2$ and 5% $CO_2$ at 37° C. in a metabolic shaker.

At the end of the time period, the metabolic products are separated on thin layer cellulose or the like, and visualized, e.g., by UV light. The plates are then scraped and the amounts of NaMN, NaAD, NAD and NADP are then determined through scintillation techniques.

Next, in a parallel run, 1.0–1000.00 $\mu$M of the material to be tested is added to the incubate described above. The procedure is repeated and the amounts of NaMN, NaAD, NAD and NADP are determined. If the determination for the test material gives a result lower than nicotinic acid, it indicates positive effectiveness. Advantageously a material to be useful for the instant treatment should show a test value at least about 5% and preferably at least about 10% inhibition of nicotinic acid metabolism.

The invention will be further described in the following illustrative examples wherein all parts are by weight unless otherwise expressed.

EXAMPLE 1

10 parts by weight of 2-fluoronicotinic acid are compounded with 2 parts by weight of silica, 2 parts by weight of $BaSO_4$ and 1 part by weight of polyvinyl pyrrolidone, all in powder form. The mass is formed into tablets weighing 1,000 mg, suitable for treating psoriasis upon oral administration of two tablets daily for one month.

EXAMPLE 2

An intravenous injectable solution in accordance with the present invention is made by dissolving 1,000 mg of 2-fluoronicotinic acid in a solution comprising 4.0 ml of water and 1.0 ml of propylene glycol at 23° C. with the pH of the resulting solution being adjusted to 7.4 with NaOH. 5 ml of the solution can be intravenously administered daily to retard hyperproliferative activity in a patient afflicted therewith.

It will be appreciated that the instant specification and claims are set forth by way of illustration and not limitation, and that various modifications and changes may be made without departing from the spirit and scope of the present invention.

What is claimed is:

1. A method for the treatment of a patient afflicted with a hyperproliferative disorder comprising administering to such patient an amount effective therefor to retard hyperproliferative activity of a compound which is an analogue of nicotinic acid and inhibits nicotinic acid metabolism in vitro in human platelets.

2. The method according to claim 1, wherein the compound is pyridine, pyrazine, 1,3,5-triazine, 1,2,4-triazine, 1,2,3-triazine, 2-pyridylcarbinol, 3-pyridylcarbinol, 3-pyridylcarboxaldehyde, 4-pyridylcarboxaldehyde, nicotinuric acid, or nicotinic acid-oxide each of which is optionally substituted wherein the substituents are amino, halo, carboxy, mercapto, and hydroxy, respective salt, ester, amide, aldehyde or alcoholic reductant products of the corresponding acid and the $C_1$–$C_{22}$ branched and unbranched ethers of said alcoholic product.

3. The method according to claim 1, wherein said compound is selected from the group consisting of 2-hydroxynicotinic acid, 4-hydroxynicotinic acid, 2-fluoronicotinic acid, 3,5-pyridyldicarboxylic acid, 4-pyridylcarboxaldehyde, 4-chloronicotinic acid, 5-hydroxynicotinic acid, 6-chloronicotinic acid, 2,3-pyridyldicarboxylic acid, 5-chloronicotinic acid, nicotinuric acid, nicotinic acid-N-oxide, ethyl-2-hydroxynicotinate, 2-hydroxynicotinamide, pyrazinoic acid and triazinoic acids, where chemically possible a 2, 4, 5 or 6-halo derivative thereof, a respective salt, ester, amide, aldehyde or alcoholic reductant product of the corresponding acid and a $C_1$–$C_{22}$ branched and unbranched hydrocarbyl ether of said alcoholic product.

4. The method according to claim 1, wherein said compound carries a halogen substituent.

5. The method according to claim 1, wherein said compound is a fluoro-substituted nicotinic acid derivative.

6. The method according to claim 1, wherein the compound is a nicotinic acid derivative substituted in the 2 or 6 position by fluorine.

7. The method according to claim 1, wherein the compound is 2-amino-4-hydroxy-nicotinic acid.

8. The method according to claim 1, wherein the hyperproliferative disorder is psoriasis, psoriatic arthritis, rheumatoid arthritis, cutaneous hyperkeratosis, inflammatory bowel disease or cancer.

9. The method according to claim 1, wherein the hyperproliferative disorder is a cancer of the gastrointestinal tract.

10. The method according to claim 1, wherein the hyperproliferative disorder is psoriasis or psoriatic arthritis.

11. A screening assay to determine whether a compound would be effective in treating a hyperproliferative disorder comprising:

(1) incubating the test compound with intact human platelets or lysates thereof in the presence of nicotinic acid and phosphoribosylpyrophosphate under conditions such that the nicotinic acid would be converted to NaMN, NaAD, NAD and NADP; and (2) determining the extent of the inhibition caused by said compound on said conversion by measuring the quantity of at least one of said product produced in the reaction and comparing this quantity against the amount of same product produced in said conversion when only nicotinic acid is present.

* * * * *